(12) United States Patent
Zhao et al.

(10) Patent No.: US 12,036,021 B2
(45) Date of Patent: Jul. 16, 2024

(54) NON-CONTACT FATIGUE DETECTION SYSTEM AND METHOD BASED ON RPPG

(71) Applicant: CENTRAL CHINA NORMAL UNIVERSITY, Hubei (CN)

(72) Inventors: Liang Zhao, Hubei (CN); Sannyuya Liu, Hubei (CN); Zongkai Yang, Hubei (CN); Xiaoliang Zhu, Hubei (CN); Jianwen Sun, Hubei (CN); Qing Li, Hubei (CN); Zhicheng Dai, Hubei (CN)

(73) Assignee: CENTRAL CHINA NORMAL UNIVERSITY, Hubei (CN)

( * ) Notice: Subject to any disclaimer, the term of this patent is extended or adjusted under 35 U.S.C. 154(b) by 0 days.

(21) Appl. No.: 18/511,919

(22) Filed: Nov. 16, 2023

(65) Prior Publication Data

US 2024/0081705 A1 Mar. 14, 2024

Related U.S. Application Data

(63) Continuation of application No. PCT/CN2023/080828, filed on Mar. 10, 2023.

(30) Foreign Application Priority Data

Jun. 20, 2022 (CN) .......................... 202210695576.9

(51) Int. Cl.
*A61B 8/14* (2006.01)
*A61B 5/00* (2006.01)
(Continued)

(52) U.S. Cl.
CPC .............. *A61B 5/16* (2013.01); *A61B 5/0205* (2013.01); *A61B 5/1176* (2013.01); *A61B 5/725* (2013.01);
(Continued)

(58) Field of Classification Search
CPC ....... A61B 5/16; A61B 5/0205; A61B 5/1176; A61B 5/725; A61B 5/726; A61B 5/7264;
(Continued)

(56) References Cited

U.S. PATENT DOCUMENTS

2021/0386307 A1 12/2021 Wu et al.
2022/0156485 A1* 5/2022 Tzvieli .................. A61B 5/163

FOREIGN PATENT DOCUMENTS

CN    111714144    9/2020
CN    112102949    12/2020
(Continued)

OTHER PUBLICATIONS

"International Search Report (Form PCT/ISA/210) of PCT/CN2023/080828", mailed on May 19, 2023, pp. 1-3.

*Primary Examiner* — Joel F Brutus
(74) *Attorney, Agent, or Firm* — JCIPRNET

(57) ABSTRACT

The present disclosure provides a non-contact fatigue detection system and method based on rPPG. The system and method adopt multi-thread synchronous communication for real-time acquisition and processing of rPPG signal, enabling fatigue status detection. In this setup, the first thread handles real-time rPPG data capture, storage and concatenation, while the second thread conducts real-time analysis and fatigue detection of rPPG data. Through a combination of skin detection and LUV color space conversion, rPPG raw signal extraction is achieved, effectively eliminating interference from internal and external environmental facial noise; Subsequently, an adaptive multi-stage filtering process enhances the signal-to-noise ratio, and a multi-dimensional fusion CNN model ensures accurate detection of respiration and heart rate. The final step involves multi-channel data fusion of respiration and heartbeats, succeeding in not only learning person-independent (Continued)

features for fatigue detection but also detecting early fatigue with very high accuracy.

16 Claims, 6 Drawing Sheets

(51) Int. Cl.
*A61B 5/0205* (2006.01)
*A61B 5/1171* (2016.01)
*A61B 5/16* (2006.01)
*G06N 3/0464* (2023.01)
*G06N 3/08* (2023.01)
*G06V 10/30* (2022.01)
*G06V 40/16* (2022.01)
*A61B 5/024* (2006.01)
*A61B 5/08* (2006.01)

(52) U.S. Cl.
CPC ............ *A61B 5/726* (2013.01); *A61B 5/7264* (2013.01); *G06N 3/0464* (2023.01); *G06N 3/08* (2013.01); *G06V 10/30* (2022.01); *G06V 40/161* (2022.01); *A61B 5/02427* (2013.01); *A61B 5/0816* (2013.01); *G06V 2201/03* (2022.01)

(58) Field of Classification Search
CPC .... A61B 5/02427; A61B 5/0816; G06N 3/08; G06N 3/0464; G06N 3/161
See application file for complete search history.

(56) References Cited

FOREIGN PATENT DOCUMENTS

| | | |
|---|---|---|
| CN | 113420624 | 9/2021 |
| CN | 114781465 | 7/2022 |

* cited by examiner

NON-CONTACT FATIGUE DETECTION SYSTEM AND METHOD BASED ON RPPG

CROSS-REFERENCE TO RELATED APPLICATION

This application is a continuation of international PCT application serial no. PCT/CN2023/080828, filed on Mar. 10, 2023, which claims priority benefit of China patent application No. 202210695576.9 filed on Jun. 20, 2022. The entirety of each of the above-mentioned patent applications is hereby incorporated by reference herein and made a part of this specification.

BACKGROUND

Technical Field

The present disclosure belongs to the field of information technology, and more specifically relates to a non-contact fatigue detection system and method based on remote photoplethysmography (rPPG).

Description of Related Art

Fatigue is not just a mere physical state; it is also an emotional state that significantly affects people's daily lives and efficiency. Extreme fatigue can have a dramatic impact on both physical and mental health. For example, driving while fatigued significantly increases the likelihood of traffic accidents. In the context of learning, fatigue not only considerably reduces learning efficiency, but also leads to distraction, slow thinking, memory loss, emotional restlessness, boredom, and irritability, and various other symptoms. These symptoms have negative effects on the learners' physiology, psychology, and cognition. Nowadays, the detection of fatigue has become a major research topic, attracting significant attention from academia and industry.

In the past, fatigue detection was primarily conducted based on conventional video analysis methods, which involved detecting fatigue status through indicators such as blink rate, yawning, napping, facial expressions, etc. Thanks to the rapid development of video detection technology, the accuracy of video-based fatigue detection has been continuously improved. However, such method also has considerable limitations, as various factors can introduce deviations in the test results: ① The subject being test may attempt to camouflage their true state (by, for example, pretending to close eyes, yawning, napping, and disguising in facial expressions, etc.); ② Variations in facial physiological characteristics (such as: size differences between eyes, etc.); ③ Fluctuations in lighting condition (such as: dim light, uneven illumination, etc.). In addition, conventional video-based analysis methods generally are able to detect the fatigue state only when the subject under test enters a relatively deep fatigue state (e.g., so sleepy with eyes closed, yawning, napping, etc.). That is to say, on the one hand, conventional video-based analysis methods cannot effectively and timely detect the early stage of fatigue state; on the other hand, after entering a relatively deep fatigue state, problems like head deflection resulting from actions such as yawning can add complexity to face tracking and fatigue detection, potentially leading to measurement errors. Therefore, conventional fatigue detection methods based on video analysis are relatively inferior in reliability and robustness.

SUMMARY

In view of the defects of related art, the purpose of the present disclosure is to provide a non-contact fatigue detection system and method based on rPPG, aiming to solve poor reliability and robustness of the conventional fatigue detection method based on video analysis.

In order to achieve the above purpose, in the first aspect, the present disclosure provides a non-contact fatigue detection method based on rPPG, and the method includes the following steps.

Determining an image video of a human face;

Performing face tracking using region-of-interest (ROI) on each image in the image video, extracting a skin binarized image of the ROI on the human face; converting each image into LUV color space image on the basis of removing the eyes and mouth regions (which are more susceptible to motion artifacts); performing an AND operation on the skin binarized image and the LUV color space image to obtain an LUV color space image that only contains human face skin information; determining the mean value of effective pixels of the LUV color space image containing only human face skin information in each image, using the mean value curve of effective pixels corresponding to the image video as the raw signal of human face remote photoplethysmography (rPPG);

Filtering the rPPG raw signal by using a first wavelet filter with a bandwidth established around a center frequency that corresponds separately to a respiration rate and a heart rate, removing noise in a coarse-grained manner, initially reconstructing respiration and heartbeat waveforms, wherein the bandwidth of the first wavelet filter is greater than a preset threshold; calculating the human body's average respiration and heartbeat intervals based on the initially reconstructed respiration and heartbeat waveforms to initially estimate the respiration and heart rate frequencies, and filtering the initially reconstructed respiration and heartbeat waveforms by using the second wavelet filter with a bandwidth set around a center frequency based on the initially estimated respiration and heart rate frequencies, removing noise in a fine-grained manner to obtain reconstructed respiration and heartbeat waveforms, wherein the bandwidth of the second wavelet filter is smaller than the bandwidth of the first wavelet filter;

Inputting the one-dimensional data of the reconstructed respiration and heartbeat waveforms into the trained one-dimensional convolutional neural network (CNN) to estimate the respiration and heart rate frequencies again; transforming the one-dimensional data of the reconstructed respiration and heartbeat waveforms by continuous wavelet transform (CWT) into two-dimensional CWT spectrograms, inputting the two-dimensional CWT spectrograms into the trained two-dimensional CNN to further estimate the respiration and heart rate frequencies; inputting the respiration and heart rate frequencies estimated by two CNNs (i.e. one-dimensional CNN and two-dimensional CNN) into the integrated learning model to determine the final respiration and heart rate frequencies;

Extracting the time-domain features, frequency-domain features and nonlinear features of the corresponding respiration and heartbeat waveforms reconstructed twice, concatenating the extracted features and the final determined respiration and heart rate frequencies and inputting them into the trained classifier, classifying the fatigue state of the human body, and detecting the fatigue state of the human body.

In an optional example, the rPPG raw signal is specifically obtained through the following steps:

Determining each image in the face image video, performing face detection and face alignment operations on each image, and extracting the ROI of human face;

Converting the RGB image in the ROI of human face in each image into YCbCr color space, and extracting the skin binarized image of the ROI of human face; wherein the skin binarized image is: setting the pixels related to the skin to 1, and setting the pixels irrelevant to the skin to 0;

With respect to each image in the image video, removing the noise irrelevant to the skin, and deleting the eyes and mouth regions of the human face (which are more susceptible to motion artifacts) based on the human face feature points, performing the conversion from the RGB image to the LUV color space, and obtaining the LUV color space image of each image;

Performing an AND operation on the skin binarized image of the ROI of face in each image and the LUV color space image of each image to obtain an LUV color space image containing only skin information;

Calculating the mean value of the effective pixels of the LUV color space image containing only skin information in each image, and using the time-series change curve of the mean value of the effective pixels as the rPPG raw signal.

In an optional example, the respiration and heartbeat waveforms are reconstructed through the following steps:

Filtering the rPPG raw signal by using the first wavelet filter, wherein the center frequencies of the respiration and heart rate are 0.3 Hz and 1.4 Hz respectively; the bandwidth center of the first wavelet filter to filter the respiration signal is the respiration center frequency, the bandwidth center for filtering the heart beat signal is the center frequency of the heart rate;

Performing the inverse continuous wavelet transform (ICWT) on the filtered respiration and heart rate signals to obtain initially reconstructed respiration and heartbeat waveforms;

On the basis of waveform peak-seeking and valley-seeking, initially estimating the respiration frequency by calculating the peak-to-peak interval of the initially reconstructed respiration waveform, calculating the peak-to-peak interval of the initially reconstructed heartbeat waveform to initially estimate the heart rate frequency;

Filtering the initially reconstructed respiration and heartbeat waveforms by using the second wavelet filter to obtain the restructured respiration and heartbeat waveforms, where the center frequencies of the two bandwidths for filtering the respiration and heartbeat waveforms correspond to the initially estimated respiration and heart rate frequencies, respectively; the two bandwidths of the second wavelet filter are respectively smaller than the two bandwidths of the first wavelet filter.

In an optional example, the final respiration and heart rate frequencies are determined through the following steps:

Normalizing the reconstructed respiration and heartbeat waveform signals to obtain the corresponding one-dimensional data;

Inputting the one-dimensional data into the trained one-dimensional CNN, and estimating the respiration and heart rate frequencies again, wherein the one-dimensional CNN includes three sub-modules: the first sub-module contains two one-dimensional convolutional layers, after each convolutional layer, the activation function (LeakyRelu), maximum pooling, and random deactivation (Dropout) operations are performed sequentially; the second sub-module is connected after the first sub-module, which contains five one-dimensional convolutional layers, after each convolutional layer, the activation function, maximum pooling, and random deactivation operations are performed sequentially; the third sub-module is connected behind the second sub-module, and after the global average pooling and random deactivation operations are performed sequentially, frequency estimation is performed through a fully connected layer containing a single neuron, and the respiration and heart rate frequencies are estimated again;

Using CWT to convert the respiration and heartbeat waveforms into two-dimensional CWT spectrograms; dividing the two-dimensional CWT spectrograms into training set and test set, and using the training set to train the top layer parameters of the two-dimensional CNN, wherein the underlying parameters of the two-dimensional CNN adopt the initial value before training, and a test set is adopted to verify the trained two-dimensional CNN's performance in identifying respiration and heart rate frequencies; the underlying parameters make full use of the extensive and rich feature representation capabilities of the two-dimensional CNN learned from millions of images; the top layer parameters are trained using the generated two-dimensional CWT spectrograms (from the training set) to estimate the respiration and heart rate frequencies based on the spectrograms (from the test set);

Inputting the respiration and heart rate frequencies estimated by the two CNNs into the integrated learning model, optimizing the respiration and heart rate frequencies, and determining the final respiration and heart rate frequencies.

In an optional example, the fatigue state of the human body is classified specifically through the following steps:

Extracting time-domain features, frequency-domain features and nonlinear features of the corresponding respiration and heartbeat waveforms reconstructed twice;

Performing feature concatenation, default value processing and feature normalization on the extracted time-domain features, frequency-domain features and nonlinear features of respiration and heartbeat waveforms with the finally determined respiration and heart rate frequencies, then using a latent semantic analysis to extract new features from the normalized features;

Inputting the new features into the fatigue classifier constructed based on XGBoost to classify the fatigue state, wherein the fatigue state is classified into three states: alertness, normal state and fatigue state, wherein alertness and normal state are both non-fatigue states.

In a second aspect, the present disclosure provides a non-contact fatigue detection system based on rPPG, and the system includes:

A human face video determination unit is configured to determine the image video of the human face;

An rPPG signal extraction unit is configured to perform face tracking using ROI on each image in the image video, extract a skin binarized image of the ROI on the face; convert each image into LUV color space image on the basis of removing the eyes and mouth regions; perform an AND operation on the skin binarized image and the LUV color space image to obtain an LUV color space image that only contains human face skin information; determine the mean value of effective pixels of the LUV color space image containing only human face skin information in each image, use the mean value curve of effective pixels corresponding to the image video as the rPPG raw signal of human face rPPG;

A waveform reconstruction unit is configured to filter the rPPG raw signal by using a first wavelet filter with a bandwidth established around a center frequency that corresponds separately to a respiration rate and a heart rate, remove noise in a coarse-grained manner, initially reconstruct respiration and heartbeat waveforms, wherein the bandwidth of the first wavelet filter is greater than a preset threshold; calculate the human body's average respiration and heartbeat intervals based on the initially reconstructed respiration and heartbeat waveforms to initially estimate the respiration and heart rate frequencies, and filter the initially reconstructed respiration and heartbeat waveforms by using the second wavelet filter with a bandwidth set around a center frequency based on the initially estimated respiration and heart rate frequencies, remove noise in a fine-grained manner to obtain reconstructed respiration and heartbeat waveforms, wherein the bandwidth of the second wavelet filter is smaller than the bandwidth of the first wavelet filter;

A frequency determination unit is configured to input the one-dimensional data of the reconstructed respiration and heartbeat waveforms into the trained one-dimensional CNN to estimate the respiration and heart rate frequencies again; transform the one-dimensional data of the reconstructed respiration and heartbeat waveforms by CWT into two-dimensional CWT spectrograms, input the two-dimensional CWT spectrograms into the trained two-dimensional CNN to further estimate the respiration and heart rate frequencies; input the respiration and heart rate frequencies estimated by two CNNs into the integrated learning model to determine the final respiration and heart rate frequencies;

A fatigue detection unit is configured to extract the time-domain features, frequency-domain features and non-linear features of the corresponding respiration and heartbeat waveforms reconstructed twice, concatenate the extracted features and the final determined respiration and heart rate frequencies and input them into the trained classifier, classify the fatigue state of the human body, and detect the fatigue state of the human body.

In an optional example, the rPPG signal extraction unit determines each image in the face image video, performs face detection and face alignment operations on each image, and extracts the ROI of face; converts the RGB image in the ROI of face in each image into YCbCr color space, and extracts the skin binarized image of the ROI of face; wherein the skin binarized image is: setting the pixels related to the skin to 1, and setting the pixels irrelevant to the skin to 0; with respect to each image in the image video, removes the noise irrelevant to the skin, and deletes the eyes and mouth regions of the face (to eliminate the motion artifacts) based on the face feature points, performs the conversion from the RGB image to the LUV color space, and obtains the LUV color space image of each image; performs an AND operation on the skin binarized image of the ROI of face in each image and the LUV color space image of each image to obtain an LUV color space image containing only skin information; and calculates the mean value of the effective pixels of the LUV color space image containing only skin information in each image, and uses the time-series change curve of the mean value of the effective pixels as the rPPG raw signal.

In an optional example, the waveform reconstruction unit filters the rPPG raw signal by using the first wavelet filter, wherein the center frequencies of the respiration and heart rate are 0.3 Hz and 1.4 Hz respectively; the bandwidth center of the first wavelet filter to filter the respiration signal is the respiration center frequency, the bandwidth center for filtering the heart beat signal is the center frequency of the heart rate; performs ICWT on the filtered respiration and heart rate signals to obtain initially reconstructed respiration and heartbeat waveforms; on the basis of waveform peak-seeking and valley-seeking, initially estimates the respiration frequency by calculating the peak-to-peak interval of the initially reconstructed respiration waveform, calculates the peak-to-peak interval of the initially reconstructed heartbeat waveform to initially estimate the heart rate frequency; and filters the initially reconstructed respiration and heartbeat waveforms by using the second wavelet filter to obtain the restructured respiration and heartbeat waveforms, where the center frequencies of the two bandwidths for filtering the respiration and heartbeat waveforms correspond to the initially estimated respiration and heart rate frequencies, respectively; the two bandwidths of the second wavelet filter are respectively smaller than the two bandwidths of the first wavelet filter.

In an optional example, the frequency determination unit normalizes the reconstructed respiration and heartbeat waveform signals to obtain the corresponding one-dimensional data; inputs the one-dimensional data into the trained one-dimensional CNN, and estimates the respiration and heart rate frequencies again, wherein the one-dimensional CNN includes three sub-modules: the first sub-module contains two one-dimensional convolutional layers, after each convolutional layer, the activation function (LeakyRelu), maximum pooling, and random deactivation (Dropout) operations are performed sequentially; the second sub-module is connected behind the first sub-module, which contains five one-dimensional convolutional layers, after each convolutional layer, the activation function, maximum pooling, and random deactivation operations are performed sequentially; the third sub-module is connected after the second sub-module, and after the global average pooling and random deactivation operations are performed sequentially, frequency estimation is performed through a fully connected layer containing a single neuron, and the respiration and heart rate frequencies are estimated again; uses CWT to convert the respiration and heartbeat waveforms into two-dimensional CWT spectrograms; divides the two-dimensional CWT spectrograms into training set and test set, and uses the training set to train the top layer parameters of the two-dimensional CNN, wherein the underlying parameters of the two-dimensional CNN adopt the initial value before training, and a test set is adopted to verify the trained two-dimensional CNN's performance in identifying respiration and heart rate frequencies; the underlying parameters make full use of the extensive and rich feature representation capabilities of the two-dimensional CNN learned from millions of images; the top layer parameters are trained using the generated two-dimensional CWT spectrograms (from the training set) to estimate the respiration and heart rate frequencies based on the spectrograms (from the test set); and inputs the respiration and heart rate frequencies estimated by the two CNNs into the integrated learning model, optimizes the respiration and heart rate frequencies, and determines the final respiration and heart rate frequencies.

In an optional example, the fatigue detection unit extracts time-domain features, frequency-domain features and non-linear features of the corresponding respiration and heartbeat waveforms reconstructed twice; performs feature concatenation, default value processing and feature normalization on the extracted time-domain features, frequency-domain features and nonlinear features of respiration and heartbeat waveforms with the finally determined respiration and heart rate frequencies, then uses a latent semantic analysis to extract new features from the normalized features; inputs the extracted features into the fatigue classifier constructed based on XGBoost, which categorizes the user's condition into two distinct states: fatigue state and non-fatigue state.

Generally speaking, compared with the related art, the above technical solution conceived by the present disclosure has the following advantageous effects.

The present disclosure provides a non-contact fatigue detection system and method based on rPPG. In terms of detection means, the present disclosure integrates the advantages of both conventional video analysis non-inductive detection and wearable device physiological signal detection, so the present disclosure is able to detect early stage of fatigue state more conveniently, more objectively and more reliably in a more timely manner. As far as the detection method is concerned, firstly, on the basis of the combination of skin detection and LUV color space conversion, rPPG original signal extraction is realized to eliminate the interference of the internal and external ambient noise of the face; secondly, signal-to-noise ratio is improved through adaptive multi-stage filtering, and high-precision detection of breathing and heart rate is achieved through multi-dimensional fusion of CNN models; finally, fatigue classification is performed on the basis of multi-channel data fusion of respiration and heart rate. In summary, the present disclosure overcomes the problem of denoising in non-contact sensing technology. On the basis of high-quality reconstruction of physiological signals and precise detection therefor, the system constructs and screens features highly related to fatigue to achieve fatigue detection with high precision and high robustness.

The disclosure provides a non-contact fatigue detection system and method based on rPPG. For non-contact fatigue detection, the advantages of the present disclosure lie in flexible and diverse detection device, objective and accurate detection results, and high detection ability in detecting minor fatigue. The above advantages make up for the shortcomings of the current detection technology, and enhance convenience and comfort of measurement, thereby providing technical support for the wide application of fatigue detection in real life.

DESCRIPTION OF THE EMBODIMENTS

Figure 1:
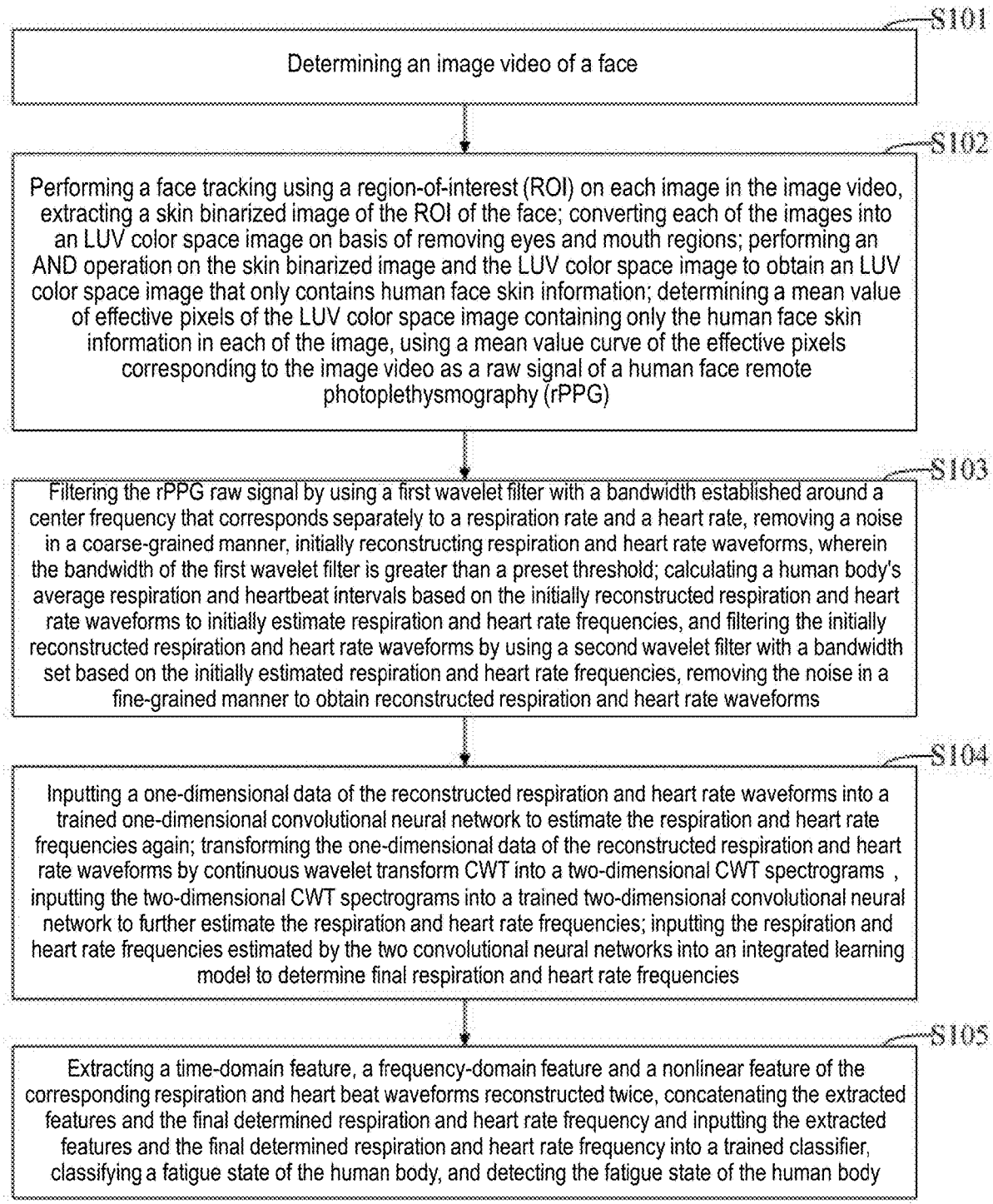
FIG. 1 is a flowchart of a non-contact fatigue detection method based on rPPG provided by an embodiment of the present disclosure.

In order to make the purpose, technical solution and advantages of the present disclosure clearer, the present disclosure will be further described in detail below in conjunction with the accompanying drawings and embodiments. It should be understood that the specific embodiments described here are only used to explain the present disclosure, not to limit the present disclosure.

Compared with conventional video analysis methods, physiological signals are less affected by subjective factors, and can objectively and truly reflect the physiological and psychological states of the subjects under test, thus receiving more attention from researchers worldwide. At present, fatigue state detection methods based on physiological signals may be categorized into contact detection and non-contact detection according to different measurement techniques and means.

On the one hand, common contact detection includes electroencephalogram (EEG), galvanic skin response (GSR), electromyogram (EMG), electrocardiogram (ECG), and photoplethysmography (PPG), etc. Such methods mostly adopt wearable devices to detect the user's fatigue state by detecting physiological signals from human organs (such as: brain, heart, etc.). Because of the advantages of long-term detection and portability, such methods have been commonly used in the laboratory environment. However, the methods also have some drawbacks. First of all, long-term wearing of the device might not only cause skin allergies or inconvenience in movement, but might also induce tension and affect test results (result from the expectation of the subjects under test). Secondly, since there is a lack of standards for wearable devices, challenges are still encountered in multi-device collaboration and real-time data collection and analysis.

On the other hand, common non-contact detection includes millimeter-wave radar and remote photoplethysmography (rPPG). In general, the rPPG method combines the advantages of objective detection of physiological signals and non-contact non-disturbance detection. Without the need for the subject under test to wear any equipment, it is possible to perform fatigue detection based on the extraction of physiological signals (such as respiration and heart beat, etc.). Furthermore, since the millimeter wave requires professional millimeter wave radar equipment to carry out relevant detection, whereas rPPG does not have any special requirements for the equipment (common mobile phones, laptops, external cameras, etc. used in daily life may be used to collect rPPG raw data), the present disclosure focuses on the study of non-contact fatigue detection system and method based on rPPG.

Specifically, rPPG is a non-contact biomedical detection technology developed on the basis of PPG. This technology uses imaging equipment to collect video information of the human body including the measured parts, and the pulse signals (namely: periodic light intensity changes caused by changes in blood volume) are recorded in the form of video images, and then pulse wave signals are extracted through video image processing, and finally physiological signals such as respiration, heart beat, blood pressure, and blood oxygen saturation are extracted through pulse wave signal analysis. From the perspective of heart rate detection, rPPG is similar to ECG/PPG, but does not require the subjects under test to wear any special equipment. Compared with conventional video analysis technology, rPPG has the following outstanding advantages. First, because the physiological signals related to the fatigue state are not related to consciousness and less easily affected by subjective intentions, the method the present disclosure is able to detect the early stage of fatigue state more objectively, and more reliably in a more timely manner. The present disclosure may not only objectively reflect the emotion, but may also detect the deliberately hidden emotional state, while being able to respond to the early symptoms and changes of human fatigue in a timely manner. Second, the method of the present disclosure may significantly reduce the impact of physiological characteristics differences in faces (such as small eyes, etc.) on the accuracy of fatigue detection. Third, the method of the present disclosure may be used for long-term monitoring of physiological signals and emotional states of telemedicine cases (such as infants, burn patients, the elderly, critically ill patients, etc.), thus effectively reducing the burden on medical staff while improving patients' comfort.

In summary, compared with conventional video analysis and wearable devices, the non-contact fatigue detection method based on rPPG has prominent advantages, such as diverse and flexible detection equipment, remote and objective detection means, and early detection capabilities for minor fatigue, etc., providing a new solution for high-accuracy fatigue state detection, and providing technical support for avoiding safety risks and health hazards that might be caused by fatigue.

FIG. 1 is a flowchart of a non-contact fatigue detection method based on rPPG provided by an embodiment of the present disclosure; as shown in FIG. 1, the method includes the following steps:

S101, determining an image video of a face;

S102, performing face tracking using region-of-interest (ROI) on each image in the image video, extracting a skin binarized image of the ROI on the face; converting each image into LUV color space image on the basis of removing the eyes and mouth regions; performing an AND operation on the skin binarized image and the LUV color space image to obtain an LUV color space image that only contains human face skin information; determining the mean value of effective pixels of the LUV color space image containing only human face skin information in each image, using the mean value curve of effective pixels corresponding to the image video as the raw signal of human face rPPG;

S103, filtering the rPPG raw signal by using a first wavelet filter with a bandwidth set based on the center frequency in conjunction with respiration and heart rate, removing noise in a coarse-grained manner, initially reconstructing respiration and heartbeat waveforms, wherein the bandwidth of the first wavelet filter is greater than a preset threshold; calculating the human body's average respiration and heartbeat intervals based on the initially reconstructed respiration and heartbeat waveforms to initially estimate the respiration and heart rate frequencies, and filtering the initially reconstructed respiration and heartbeat waveforms by using the second wavelet filter with a bandwidth set around a center frequency based on the initially estimated respiration and heart rate frequencies, removing noise in a fine-grained manner to obtain reconstructed respiration and heartbeat waveforms, wherein the bandwidth of the second wavelet filter is smaller than the bandwidth of the first wavelet filter;

S104, inputting the one-dimensional data of the reconstructed respiration and heartbeat waveforms into the trained one-dimensional convolutional neural network (CNN) to estimate the respiration and heart rate frequencies again; transforming the one-dimensional data of the reconstructed respiration and heartbeat waveforms by CWT into two-dimensional CWT spectrograms, inputting the two-dimensional CWT spectrograms into the trained two-dimensional CNN to further estimate the respiration and heart rate frequencies; inputting the respiration and heart rate frequencies estimated by two CNNs into the integrated learning model to determine the final respiration and heart rate frequencies;

S105, extracting the time-domain features, frequency-domain features and nonlinear features of the corresponding respiration and heartbeat waveforms reconstructed twice, concatenating the extracted features and the final determined respiration and heart rate frequencies and inputting them into the trained classifier, classifying the fatigue state of the human body, and detecting the fatigue state of the human body.

Figure 2:
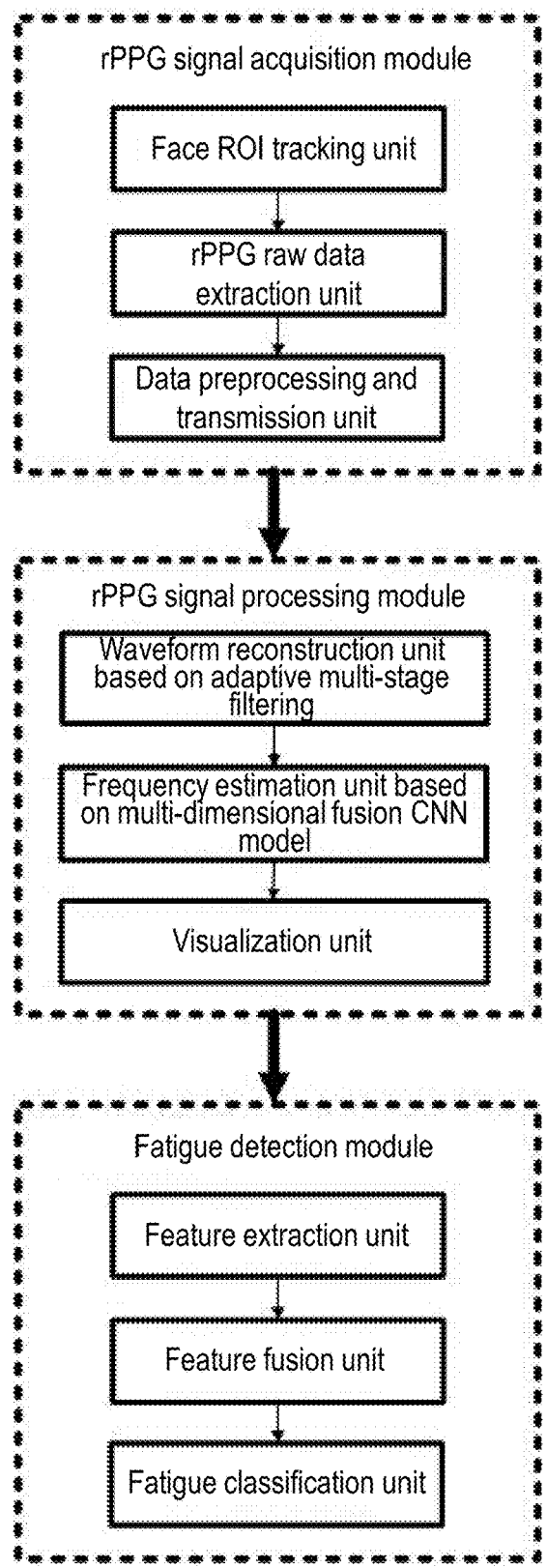
FIG. 2 is a non-contact fatigue detection block diagram based on rPPG provided by an embodiment of the present disclosure.

Specifically, the system and method provided in the present disclosure adopt multi-thread synchronous communication, and realize real-time acquisition of rPPG signal and real-time detection of fatigue state based on python threading multi-thread module. Specifically, the first thread realizes real-time capture, storage and concatenation of rPPG data; the second thread realizes real-time analysis and fatigue detection of rPPG data. FIG. 2 is a non-contact fatigue detection block diagram based on rPPG provided in an embodiment of the present disclosure, as shown in FIG. 2, the system provided in the present disclosure includes three modules:

An rPPG signal acquisition module is configured to extract the rPPG raw signal from each image, and after the preprocessing operation is performed in the sliding window, the signal is transmitted to the rPPG signal processing module;

An rPPG signal processing module is configured to receive the rPPG raw signal, extract respiration and heartbeat waveform signals through adaptive multi-stage filtering, realize high-accuracy detection of respiration and heart rate through multi-dimensional fusion CNN model, and display respiration and heartbeat waveforms in real time by means of visualization and the frequency thereof;

A fatigue detection module is configured to receive respiration and heartbeat waveform data, perform time-domain, frequency-domain and nonlinear feature extraction and feature fusion operations thereof, and construct a classifier through XGBoost to perform binary classification on fatigue and non-fatigue states.

Figure 3:
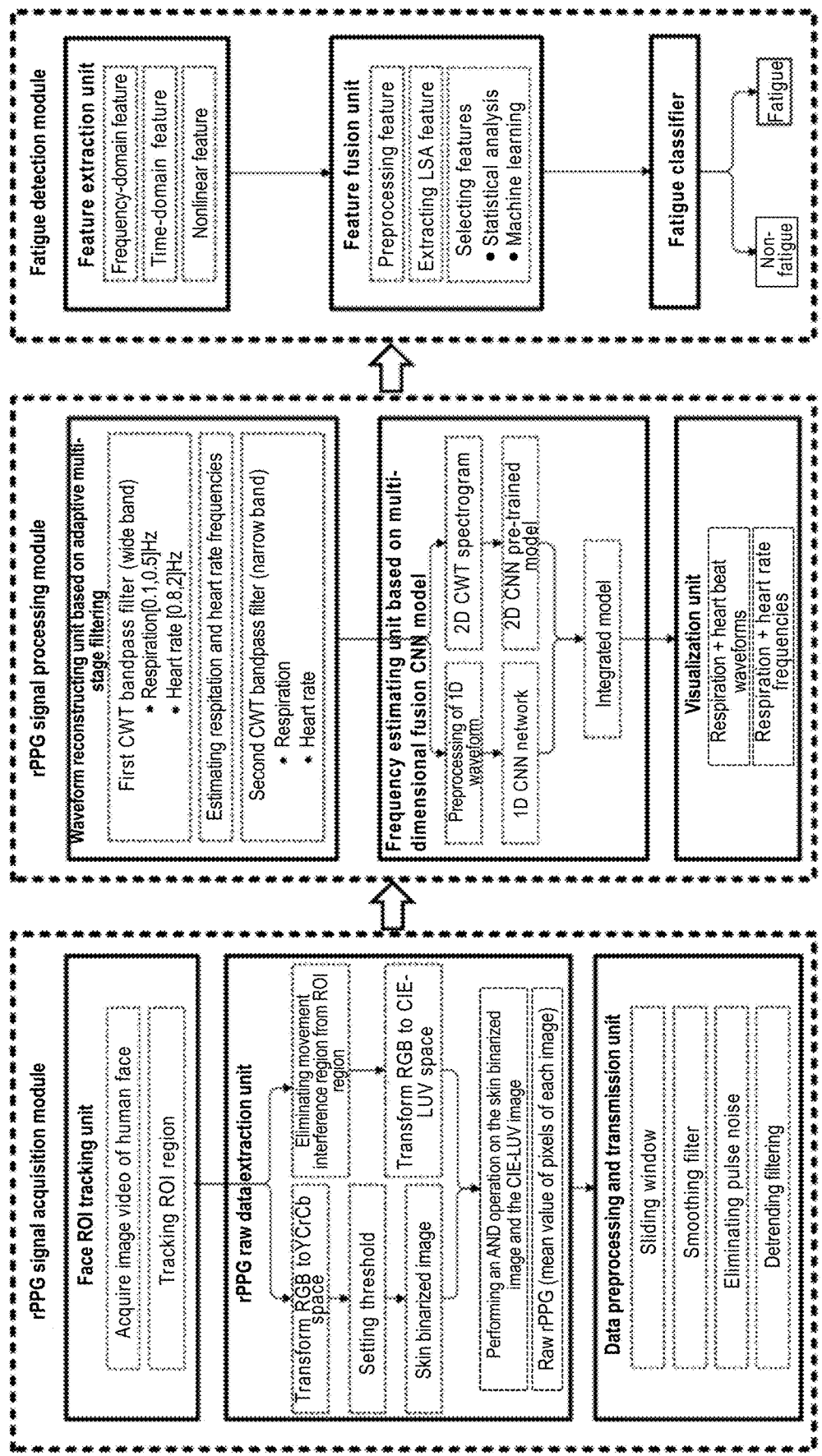
FIG. 3 is a flowchart of non-contact fatigue detection based on rPPG provided by an embodiment of the present disclosure.

The disclosure provides a non-contact fatigue detection system and method based on rPPG. The system and method adopt multi-thread synchronous communication, and realize real-time acquisition and processing of rPPG signals and synchronous detection of fatigue state based on python threading multi-thread module to meet the real-time detection requirements. The first thread realizes real-time capture, storage and concatenation of rPPG data; the second thread realizes real-time analysis and fatigue detection of rPPG data. As shown in FIG. 3, the system and method provided in the present disclosure include three modules:

First, the rPPG signal acquisition module is configured to track the ROI region of face; remove the noise interference inside and outside the face and extract the rPPG raw signal through skin detection and color space conversion; perform rPPG signal preprocessing operations, and transmit the preprocessed signal to real-time rPPG signal processing module. The module consists of three units:

① Face ROI tracking unit. First, the face ROI tracking unit obtains the capture frame rate of the video capture device and the resolution of each image; monitors the video capture device and captures each image in real time. Secondly, face detection is performed based on the Viola-Jones algorithm, and face alignment is performed based on the FaceAligner of the Python imutils library, and face feature point tracking is performed based on the frontal_face_detector of Python dlib (that is: extract 68 feature points of the face, including: eyebrows, eyes, nose, mouth and contour of face, etc.).

② The rPPG raw data extraction unit. First, the RGB image in the ROI region of face is subjected to YCbCr space conversion, and three channel thresholds Y, Cb and Cr are established:

$$\begin{cases} Y > 80 \\ 77 < Cb < 127 \\ 133 < Cr < 173 \end{cases} \quad (1)$$

The image is converted into a binary image based on the threshold (i.e., extract the skin information of the ROI region of the face, set the pixels related to the skin to 1, and set the pixels not related to the skin to 0), and the noise that has nothing to do with the skin is removed (e.g., hair reflections from within the ROI region). Secondly, based on the feature points of the face, the eyes and mouth regions of the face are deleted, and the conversion from RGB to LUV color space is performed to remove noise interference such as motion. Thirdly, "AND" operation is performed on the skin binary image and the LUV image to obtain a color image containing only skin information. The mean value of effective pixels in each image is calculated, and the time-series change curve of the mean value serves as the rPPG raw signal.

③ The data preprocessing and transmission unit. A sliding window is set to perform preprocessing operations on the data in the window (including: impulse noise elimination, detrending filtering and smoothing filtering), and new data is periodically transmitted to the rPPG signal processing module.

Second, the rPPG signal processing module reconstructs respiration and heartbeat waveform signals through adaptive multi-stage filtering, estimates respiration and heart rate through multi-dimensional fusion CNN model, and displays respiration and heartbeat waveforms and frequency values thereof in real time through visualization. The module consists of three units:

① A waveform reconstruction unit based on adaptive multi-stage filtering. Adaptive multi-stage filtering is adopted to remove out-of-band noise at a coarse-grained and fine-grained level, respectively, and realize the reconstruction of respiration and heartbeat waveforms. The specific steps are as follows. First, continuous wavelet transform (CWT) is adopted, and in the wavelet domain, wavelet filters with wide bandwidth are adopted ([0.1, 0.5] Hz and [0.8, 2.0] Hz band-pass filters are adopted respectively for filtering respiration and heartbeat waveform signals), out-of-band noise is removed in a coarse-grained level, and respiration and heartbeat waveform signals are reconstructed initially:

$$\begin{cases} x_{b0}(n) = ICWT\left\{\sum_{0.1}^{0.5} CWT\{x(n)\}\right\} \\ x_{h0}(n) = ICWT\left\{\sum_{0.8}^{2.0} CWT\{x(n)\}\right\} \end{cases} \quad (2)$$

The filter bandwidth used here is relatively wide, where the center frequencies of respiration and heart rate are 0.3 Hz and 1.4 Hz, respectively, and the half bandwidths (HBW) thereof are respectively $f_{HBW\_b0}$=0.2 Hz and $f_{HBW\_h0}$=0.6 Hz; inverse continuous wavelet transform (ICWT) is performed to obtain the reconstructed respiration and heartbeat waveforms which are denoted as $x_{b0}(n)$ and $x_{h0}(n)$ respectively. Then, on the basis of waveform peak-seeking and valley-seeking, the respiration and heartbeat frequencies are initially estimated by calculating the average heartbeat interval (IBI), which are recorded as $f_{br0}$ and $f_{hr0}$, respectively. Finally, a wavelet filter with narrow bandwidth is used to remove out-of-band noise in a fine-grained level to realize the reconstruction of respiration and heartbeat waveforms:

$$\begin{cases} x_b(n) = ICWT\left\{\sum_{f_{br0}-f_{HBW\_b1}}^{f_{br0}+f_{HBW\_b1}} CWT\{x_{b0}(n)\}\right\} \\ x_h(n) = ICWT\left\{\sum_{f_{hr0}-f_{HBW\_h1}}^{f_{hr0}+f_{HBW\_h1}} CWT\{x_{h0}(n)\}\right\} \end{cases} \quad (3)$$

That is: the narrowband bandpass filter is carried out in the wavelet domain, the center frequencies of the respiration and the heart rate frequencies are respectively $f_{br0}$ and $f_{hr0}$, and the half bandwidths thereof are $f_{HBW\_b1} < f_{HBW\_b0}$=0.2 Hz and $f_{HBW\_h1} < f_{HBW\_h0}$=0.6 Hz respectively.

Figure 4:
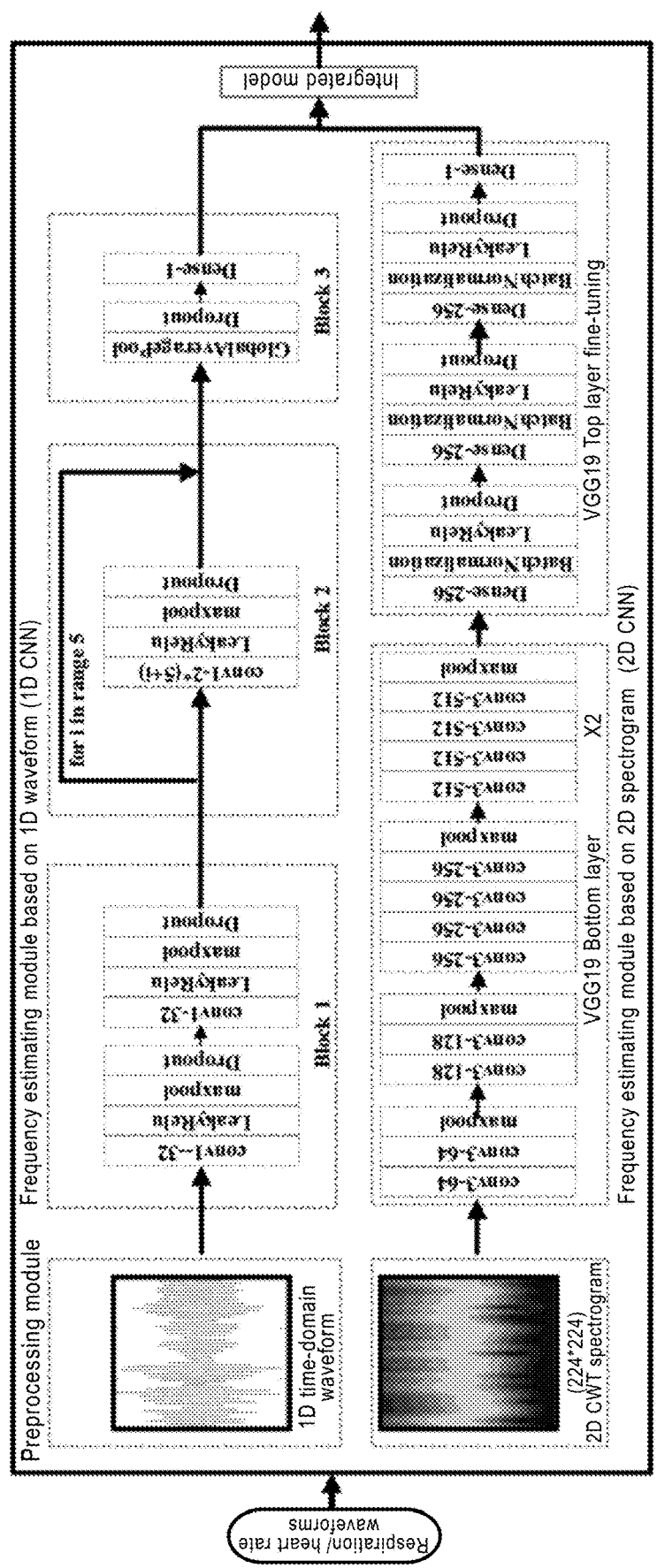
FIG. 4 is a multi-dimensional fusion CNN model diagram provided by an embodiment of the present disclosure.

② A frequency estimation unit based on multi-dimensional fusion CNN model. As shown in FIG. 4, the present disclosure performs frequency estimation based on 1D respiration and heartbeat waveforms and 2D spectrograms thereof respectively, and uses an integrated algorithm to further improve the performance of the frequency estimation algorithm. First, preprocessing operations are performed on the 1D waveform data of respiration and heartbeat waveforms to normalize the signal to [−1,1]; the preprocessed waveforms are input into the one-dimensional CNN network, which contains three sub-modules: Block 1~Block 3. Specifically, in Block 1 and Block 2, after each one-dimensional CNN layer, there is a series of LeakyRelu, maxpool and Dropout operations. In Block 1, each one-dimensional CNN layer consists of 32 neurons; and in Block 2, the five one-dimensional CNN layers consist of 2*(5+i) neurons, 0≤i≤4. In Block 3, after the GlobalAveragePool and Dropout operations, there is a fully connected layer containing 1 neuron, which is used for frequency estimation, and the estimated frequencies of respiration and heart rate are denoted as $f_{br1\_1d}$ and $f_{hr1\_1d}$, respectively. Secondly, CWT is adopted to convert the 1D waveform data of respiration and heartbeat waveforms into 2D CWT spectrograms. The 2D CWT spectrograms are divided into a training set and a test set, and the training set is utilized to train the top layer parameters of the pre-trained model of the 2D CNN classic network (such as: VGG19) (the underlying bottom layers parameters remain unchanged, that is, the initial value in the pre-trained model is adopted), and the test set is utilized to verify the performance of the model for recognizing respiration and heart rate frequency.

That is to say, on the one hand, the underlying parameters make full use of the extensive and rich feature representation capabilities learned by the pre-trained model from millions of images; on the other hand, the top layer are trained using the generated two-dimensional CWT spectrograms (from the training set) to estimate the respiration and heart rate frequencies based on the spectrograms (from the test set). The estimated frequencies of respiration and heart rate thereof are denoted as $f_{br1\_2d}$ and $f_{hr1\_2d}$, respectively. Finally, the frequency estimates of 1D CNN and 2D CNN approaches are input into the integrated learning model (such as: SGD regression model) to optimize the frequency estimates. The estimated frequencies of respiration and heart rate frequencies are denoted as $f_{br2}$ and $f_{hr2}$, respectively.

③ Visualization unit is configured to visualize real-time respiration and heartbeat waveforms and frequency estimation results thereof.

Thirdly, the fatigue detection module fuses multi-channel data of respiration and heart beat, performs feature extraction and feature fusion, and constructs a classifier through XGBoost to perform binary classification on fatigue and non-fatigue states. The module consists of three units:

① Feature extraction unit. Respiration and heart beat features are extracted from three perspectives, namely: time-domain, frequency-domain and nonlinear features. Specifically, firstly, the spectral power ratio feature is extracted from the respiration and heartbeat waveforms; secondly, the time-domain feature is extracted, and after the peaks of the respiration and heartbeat waveforms are detected, the peak-to-peak interval sequence is calculated. With respect to the heartbeat waveform, heart rate (HR) and heart rate variability (HRV) related time-domain features are extracted on basis of the time series of HR and HRV generated by using the peak-to-peak interval sequence; and the lag time (lag, that is, the autocorrelation function drops to the initial 1−1/e) and mean period (that is, the reciprocal of the average frequency of the power spectrum), see Table 1. Thirdly, nonlinear features are extracted, including turning points ratio (tpr), modified turning points ratio (mtpr), improved Shannon Entropy, refined composite multiscale entropy (rcmse), sample Entropy, Lyapunov Exponent, Hurst Exponent and Detrended Fluctuation Analysis (DFA) index.

Specifically, the time-domain and frequency-domain features are calculated mainly using six Python libraries: scipy, biosppy, heartpy, ppg45, pyHRV, and hrvanalysis; while the nonlinear features are calculated using Python's nolds library. Further, with respect to the input respiration/heartbeat waveform sequence x (the number of samples is N):

$$rcmse(x, \tau, m, r) = -\ln\left(\frac{\overline{n}_{k,\tau}^{m+1}}{\overline{n}_{k,\tau}^{m}}\right) = -\ln\left(\frac{\sum_{k=1}^{\tau} n_{k,\tau}^{m+1}}{\sum_{k=1}^{\tau} n_{k,\tau}^{m}}\right) \quad (5)$$

In the formula $$\overline{n}_{k,\tau}^{m+1} = \frac{1}{\tau}\sum_{k=1}^{\tau} n_{k,\tau}^{m+1}; \overline{n}_{k,\tau}^{m} = \frac{1}{\tau}\sum_{k=1}^{\tau} n_{k,\tau}^{m},$$

that is $\overline{n}_{k,\tau}^{m+1}$ and $\overline{n}_{k,\tau}^{m}$ are respectively the mean values of $\tau$ $n_{k,\tau}^{m+1}$ and $n_{k,\tau}^{m}$ when $1 \leq k \leq \tau$.

The calculation of tpr is as follows:

$$tpr = \frac{\sum_{i=2}^{N-1}[(x_i - x_{i-1})(x_i - x_{i+1}) > 0]}{N - 2} \quad (6)$$

The calculation of mtpr is as follows. First, the trend of the input sequence x is extracted by using empirical mode decomposition (EMD); then, the coarse-grained process of the trend sequence is calculated, as shown in formula (4); finally, the mtpr of the coarse-grained process is calculated, as shown in formula (6).

TABLE 1

Respiration and heart beat feature extraction based on rPPG

| Data | Type of Features | Name of Features |
|---|---|---|
| Respiration | Time-domain | bpm, ibi, sdnn, sdsd, rmssd, pnn20, pnn50, mad, sd1, sd2, s, sd1/sd2; ppg45 features (39); sdRate, TINN |
| | | lag, mean period |
| | Frequency-domain | ppg45 feature(6) |
| | Nonlinear | Shannon entropy, rcmse, sample entropy, Lyapunov Exponent, Hurst Exponent, DFA |
| Heart Rate | Time-domain | HR & HRV feature: mean, std (standard deviation), skewness, kurtosis, percentage of points higher than mean + std, and percentage of points lower than mean − std |
| | | HeartPy feature: bpm, ibi, sdnn, sdnni, sdsd, rmssd, pnn20, pnn50, nn50, mad, sd1, sd2, s, sd1/sd2 |
| | | ppg45 feature(39) |
| | | Waveform-related features: tpr, mtpr |
| | | lag, mean period |
| | Frequency-domain | Power spectrum & Power ratio: 0-6 Hz (per 0.1 Hz), LF, MF, HF, TF, LF/HF, LF/TF, HF/TF, LF/(TF-LF), HF/(TF-LF), peakLF, peakHF, HF/(TF-LF) |
| | | ppg45 feature(6): $f_{base}$, $|S_{base}|$, $f_2$, $|S_2|$, $f_3$, $|S_3|$ |
| | Nonlinear | Shannon entropy, rcmse, sample entropy, Lyapunov Exponent, Hurst Exponent, DFA |

RCMSE is calculated as follows. First, the coarse-grained process at the $\tau^{th}$ scale of the input sequence x is calculated as follows:

$$y_{k,j}^{(\tau)} = \frac{1}{\tau}\sum_{i=(j-1)\tau+k}^{j\tau+k-1} x_i, 1 \leq j \leq \frac{N}{\tau}, 1 \leq k \leq \tau \quad (4)$$

Next, under the scale factor $\tau$, the number of matching vector pairs $n_{k,\tau}^{m+1}$ and $n_{k,\tau}^{m}$ of all $\tau$ coarse-grained sequences is calculated; finally, the rcmse under the scale factor $\tau$ is calculated:

It should be noted that (i) low frequencies (LF, 0.01 to 0.08 Hz); medium frequencies (MF, 0.08 to 0.15 Hz); high frequencies (HF, 0.15 to 0.50 Hz); total frequencies (TF, 0.01 to 0.50 Hz); (ii) ppg45 features (39): x, y, z, y/x, (x−y)/x, z/x, (y−z)/x, w, $A_2/A_1$, $t_{pi}$, $t_1$, $t_2$, $t_3$, $\Delta T$, $t_1/t_{pi}$, $t_2/t_{pi}$, $t_3/t_{pi}$, $\Delta T/t_{pi}$, $t_{a1}$, $t_{b1}$, $t_{e1}$, $t_{f1}$, $b_2/a_2$, $e_2/a_2$, $(b_2+e_2)/a_2$, $t_{a2}$, $t_{b2}$, $t_{a1}/t_{pi}$, $t_{b1}/t_{pi}$, $t_{e1}/t_{pi}$, $t_{f1}/t_{pi}$, $t_{a2}/t_{pi}$, $t_{b2}/t_{pi}$, $(t_{a1}-t_{a2})/t_{pi}$, $(t_{b1}-t_{b2})/t_{pi}$, $(t_{e1}-t_2)/t_{pi}$, $(t_{f1}-t_3)/t_{pi}$, $t_1/x$, $y/(t_{pi}-t_3)$, svri.

② Secondly, a feature fusion unit. Firstly, feature preprocessing is performed, mainly including feature concatenation, default value processing and feature normalization. Specifically, in feature concatenation, (i) the time-domain, frequency-domain and nonlinear features (extracted from the waveform reconstruction unit of adaptive multi-stage filtering based on respiration and heartbeat waveforms reconstructed twice respectively) and (ii) the final respiration and heart rate frequencies (calculated by the multi-dimensional fusion CNN model unit) are spliced together. Secondly, latent semantic analysis (LSA) is adopted to extract new features. Finally, statistical analysis and machine learning algorithms are combined to screen for features highly correlated with fatigue.

Figure 5:
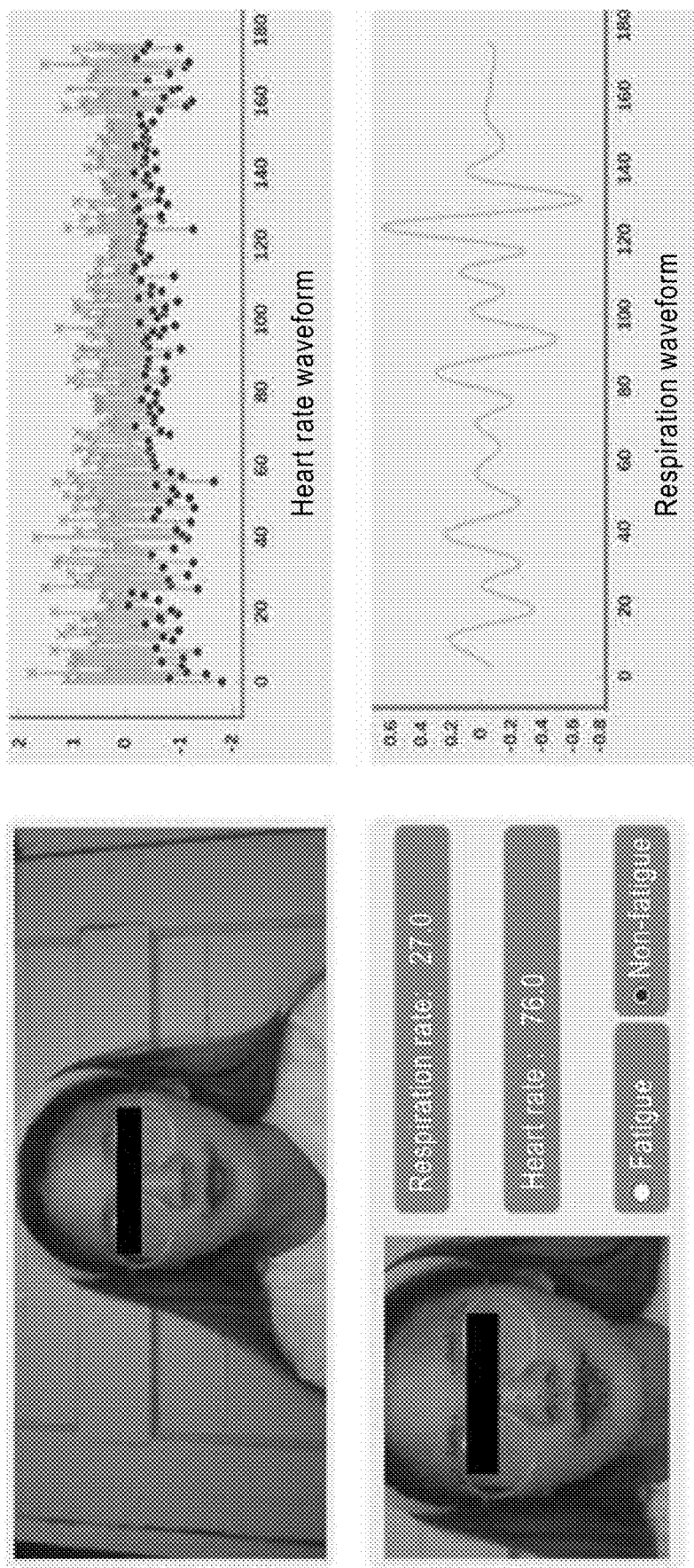
FIG. 5 is a visual interface diagram provided by an embodiment of the present disclosure.

③ Thirdly, a fatigue classification unit. A fatigue classifier is constructed based on XGBoost, and the selected features are input into the classifier to realize fatigue state classification and visualization, as shown in FIG. 5.

In order to verify the effectiveness of the system and method provided in the present disclosure, the present disclosure performs verification on a self-built data set. In the process of frequency detection and fatigue detection, the relevant data is segmented into 30 seconds in the data set. The comparison experiment results of heart rate estimation accuracy are shown in Table 2 and Table 3; 10-fold cross-validation and leave-one-out cross-validation of fatigue detection verification test results are shown in Table 4 and Table 5.

PSD), the heart rate estimation algorithm based on the time-domain (peak-seeking and valley-seeking algorithm) has higher accuracy.

TABLE 3

Heart rate estimation results based on multi-dimensional fusion CNN model

| DL methods | MAE (bpm) | SD (bpm) | RMSE (bpm) | Pearson Correlation (r < 0.05) |
|---|---|---|---|---|
| CorNET | 2.545 | 2.876 | 3.673 | 0.905 |
| Proposed | 2.034 | 2.626 | 3.320 | 0.927 |

The heart rate estimation results based on the multi-dimensional fusion CNN model are shown in Table 3. First, as can be seen from Table 3, compared with the classic time series estimation algorithm CorNET network, the heart rate estimation effect of the model provided in the present disclosure is better. Secondly, compared with Table 2, it can

TABLE 2

Comparison of heart rate estimation results before and after adaptive multi-stage filtering

| Color channel | Filtering method | Frequency Domain (PSD) | | | | Time Domain (Peak-Seeking and Valley-Seeking algorithm) | | | |
|---|---|---|---|---|---|---|---|---|---|
| | | MAE (bpm) | SD (bpm) | RMSE (bpm) | Pearson Correlation (r < 0.05) | MAE (bpm) | SD (bpm) | RMSE (bpm) | Pearson Correlation (r < 0.05) |
| Green | ① Primary filtering | 5.659 | 8.189 | 9.947 | 0.528 | 3.660 | 4.301 | 5.643 | 0.782 |
| | ② Adaptive multi-stage filtering | 4.084 | 5.583 | 6.913 | 0.741 | 3.214 | 4.425 | 5.465 | 0.810 |
| ICA | ① Primary filtering | 5.041 | 7.592 | 9.106 | 0.592 | 3.831 | 4.598 | 5.981 | 0.776 |
| | ② Adaptive multi-stage filtering | 3.993 | 5.807 | 7.042 | 0.720 | 3.698 | 4.852 | 6.097 | 0.762 |
| Skin detection + LUV | ① Primary filtering | 3.259 | 5.008 | 5.971 | 0.813 | 2.551 | 3.240 | 4.121 | 0.891 |
| | ② Adaptive multi-stage filtering | 2.795 | 3.946 | 4.835 | 0.869 | 2.077 | 2.903 | 3.569 | 0.918 |

As far as data collection is concerned, on the one hand, the self-built data set used the Karolinska sleepiness scale (KSS) to collect the learning status in the natural learning environment. On the other hand, OPPO R9 and other mobile phones and Inspiron 5598 and other laptops were utilized to collect rPPG data of 12 students (no special requirements were set for equipment in the collection and analysis process) in fatigue and non-fatigue states, and each data lasted 10 minutes. Since no additional experimental stimuli (such as sleep deprivation experiments, etc.) were applied during the experiment, the measured fatigue states were all relatively mild early fatigue (under the fatigue state, KSS mean value=7.417).

As far as frequency detection is concerned, the present disclosure achieves high-quality reconstruction of respiration and heart beat through adaptive multi-stage filtering. Specifically, taking heart rate estimation as an example, The comparison of experimental results before and after adaptive filtering is shown in Table 2. It can be seen from the table: First, among the rPPG signal extraction methods in three different color spaces (Green channel, ICA and "Skin detection+LUV"), the "Skin detection+LUV" method used in this study has the highest accuracy; secondly, among the three color space methods, adaptive multi-stage filtering can effectively improve the accuracy of heart rate detection. In addition, compared with the heart rate estimation algorithm based on the frequency-domain (power spectral density, be seen that the multi-dimensional fusion CNN model provided in the present disclosure can significantly improve the performance of the heart rate estimation algorithm.

TABLE 4

Fatigue detection results (10-fold cross-validation)

| Feature | Accuracy | Precision | F1 Score | AUC |
|---|---|---|---|---|
| Respiration | 0.627 | 0.640 | 0.626 | 0.628 |
| Heart Rate | 0.871 | 0.881 | 0.871 | 0.874 |
| Respiration + Heart Rate | 0.900 | 0.903 | 0.900 | 0.901 |

TABLE 5

Fatigue detection results (leave-one-out cross-validation)

| Feature | Accuracy | Precision | F1 Score | AUC |
|---|---|---|---|---|
| Respiration | 0.629 | 0.664 | 0.632 | 0.638 |
| Heart Rate | 0.800 | 0.827 | 0.803 | 0.797 |
| Respiration + Heart Rate | 0.817 | 0.835 | 0.818 | 0.814 |

As far as fatigue detection is concerned, it can be seen from Tables 4 and 5 that the system and method provided by the present disclosure may accurately detect the early stage of fatigue state. Taking the accuracy rate as an example, the accuracy rates of the 10-fold cross-validation method and the leave-one-out method cross-validation respectively reached 90.0% and 81.7%. Specifically, 1) The performance of fatigue detection may be improved through the fusion of multi-channel data of respiration and heart beat. 2) Further, from the leave-one-out cross-validation in Table 5, it can be seen that, in the non-contact fatigue detection system and method based on rPPG provided in the present disclosure, the features learned in the known subject (/under test) may be well transferred to the fatigue detection applications of the unknown subject, and has good robustness and transferability.

Figure 6:
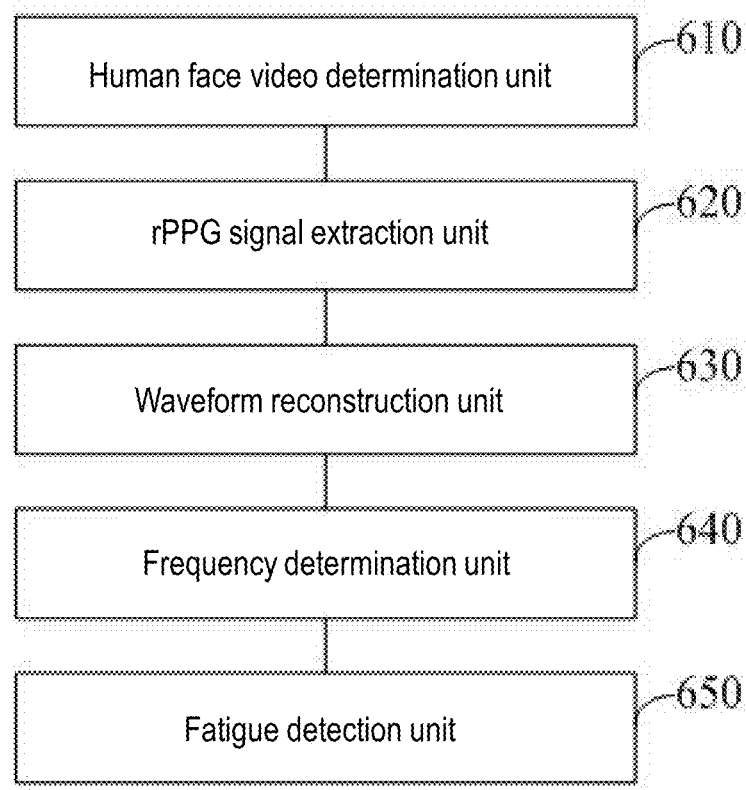
FIG. 6 is an architecture diagram of a non-contact fatigue detection system based on rPPG provided by an embodiment of the present disclosure.

FIG. 6 is an architecture diagram of a non-contact fatigue detection system based on rPPG provided by an embodiment of the present disclosure. As shown in FIG. 6, the system includes the following:

A human face video determination unit 610 is configured to determine the image video of the human face;

An rPPG signal extraction unit 620 is configured to perform face tracking using region-of-interest (ROI) on each image in the image video, extract a skin binarized image of the ROI on the face; convert each image into LUV color space image on the basis of removing the eyes and mouth regions; perform an AND operation on the skin binarized image and the LUV color space image to obtain an LUV color space image that only contains human face skin information; determine the mean value of effective pixels of the LUV color space image containing only human face skin information in each image, use the mean value curve of effective pixels corresponding to the image video as the raw signal of human face rPPG;

A waveform reconstruction unit 630 is configured to filter the rPPG raw signal by using a first wavelet filter with a bandwidth established around a center frequency that corresponds separately to a respiration rate and a heart rate, remove noise in a coarse-grained manner, initially reconstruct respiration and heartbeat waveforms, wherein the bandwidth of the first wavelet filter is greater than a preset threshold; calculate the human body's average respiration and heartbeat intervals based on the initially reconstructed respiration and heartbeat waveforms to initially estimate the respiration and heart rate frequencies, and filter the initially reconstructed respiration and heartbeat waveforms by using the second wavelet filter with a bandwidth set around a center frequency based on the initially estimated respiration and heart rate frequencies, remove noise in a fine-grained manner to obtain reconstructed respiration and heartbeat waveforms, wherein the bandwidth of the second wavelet filter is smaller than the bandwidth of the first wavelet filter;

A frequency determination unit 640 is configured to input the one-dimensional data of the reconstructed respiration and heartbeat waveforms into the trained one-dimensional CNN to estimate the respiration and heart rate frequencies again; transform the one-dimensional data of the reconstructed respiration and heartbeat waveforms by CWT into two-dimensional CWT spectrograms, input the two-dimensional CWT spectrograms into the trained two-dimensional CNN to further estimate the respiration and heart rate frequencies; input the respiration and heart rate frequencies estimated by two CNNs into the integrated learning model to determine the final respiration and heart rate frequencies;

A fatigue detection unit 650 is configured to extract the time-domain features, frequency-domain features and nonlinear features of the corresponding respiration and heart beat based on the corresponding respiration and heartbeat waveforms reconstructed twice, concatenate the extracted features and the final determined respiration and heart rate frequencies and input them into the trained classifier, classify the fatigue state of the human body, and detect the fatigue state of the human body.

It should be noted that, for the detailed realization of function of each unit in FIG. 6, reference may be made to the description in the foregoing method embodiments, and details are not repeated here.

It is easy for those skilled in the art to understand that the above descriptions are only preferred embodiments of the present disclosure, and are not intended to limit the present disclosure. Any modifications, equivalent replacements and improvements made within the spirit and principles of the present disclosure should all be included within the protection scope of the present disclosure.

What is claimed is:

1. A non-contact fatigue detection method based on rPPG (remote photoplethysmography), comprising the following steps:

determining an image video of a human face;

performing a human face tracking using a region-of-interest (ROI) on each of images in the image video, extracting a skin binarized image of a ROI of the human face; converting each of the images into an LUV color space image on basis of removing eyes and mouth regions; performing an AND operation on the skin binarized image and the LUV color space image to obtain an LUV color space image containing only human face skin information; determining a mean value of effective pixels of the LUV color space image containing only the human face skin information in each of the images, using a mean value curve of the effective pixels corresponding to the image video as a raw signal of a human face rPPG;

filtering an rPPG raw signal by using a first wavelet filter with a bandwidth established around a center frequency that corresponds separately to a respiration rate and a heart rate, removing a noise in a coarse-grained manner, initially reconstructing respiration and heart rate waveforms, wherein the bandwidth of the first wavelet filter is greater than a preset threshold; calculating a human body's average respiration and heartbeat intervals based on initially reconstructed respiration and heart rate waveforms to initially estimate respiration and heart rate frequencies, and filtering the initially reconstructed respiration and heart rate waveforms by using a second wavelet filter with a bandwidth set based on the respiration and heart rate frequencies, which are initially estimated, removing the noise in a fine-grained manner to obtain reconstructed respiration and heart rate waveforms, wherein the bandwidth of the second wavelet filter is smaller than the bandwidth of the first wavelet filter;

inputting one-dimensional data of the reconstructed respiration and heart rate waveforms into a trained one-dimensional convolutional neural network (CNN) to estimate the respiration and heart rate frequencies again; transforming the one-dimensional data of the reconstructed respiration and heart rate waveforms by continuous wavelet transform (CWT) into two-dimensional CWT spectrograms, inputting the two-dimensional CWT spectrograms into a trained two-dimensional CNN to further estimate the respiration and heart rate frequencies; inputting the respiration and heart rate frequencies estimated by two CNNs into an integrated learning model to determine final respiration and heart rate frequencies;

extracting a time-domain feature, a frequency-domain feature and a nonlinear feature of the corresponding respiration and heart rate waveforms reconstructed twice, concatenating extracted features and a final determined respiration and heart rate frequency and inputting the extracted features and the final determined respiration and heart rate frequency into a trained classifier, classifying a fatigue state of a human body, and detecting the fatigue state of the human body.

2. The method according to claim 1, wherein the rPPG raw signal is specifically obtained through the following steps:

determining each of the images in the image video of the human face, performing a human face detection and a human face alignment operation on each of the images, and extracting the ROI of the human face;

converting a RGB image in the ROI of the human face in each of the images into a YCbCr color space, and extracting the skin binarized image of the ROI of the human face; wherein the skin binarized image is: setting pixels related to skin to 1, and setting pixels, which are not related to the skin, to 0;

with respect to each of the images in the image video, removing noises, which are not related to the skin, and deleting the eyes and mouth regions of the human face based on human face feature points, performing a conversion from the RGB image to the LUV color space, and obtaining an LUV color space image of each of the images;

performing the AND operation on the skin binarized image of the ROI of the human face in each of the images and the LUV color space image of each of the images to obtain the LUV color space image containing only the skin information;

calculating the mean value of the effective pixels of the LUV color space image containing only the skin information in each of the images, and using a time-series change curve of the mean value of the effective pixels as the rPPG raw signal.

3. The method according to claim 2, wherein the respiration and heart rate waveforms are reconstructed specifically as follows:

filtering the rPPG raw signal by using the first wavelet filter, wherein the center frequencies of the respiration and heart rate are 0.3 Hz and 1.4 Hz, respectively; a bandwidth center of the first wavelet filter to filter a respiration signal is a respiration center frequency, a bandwidth center for filtering a heart rate signal is a center frequency of the heart rate;

performing ICWT on the filtered respiration and heart rate signals to obtain the initially reconstructed respiration and heart rate waveforms;

on basis of waveform peak-seeking and valley-seeking, initially estimating the respiration frequency by calculating a peak-to-peak interval of the initially reconstructed respiration waveform, calculating a peak-to-peak interval of the initially reconstructed heart rate waveform to initially estimate the heart rate frequency;

filtering the initially reconstructed respiration and heart rate waveforms by using the second wavelet filter to obtain the restructured respiration and heart rate waveforms, wherein center frequencies of two bandwidths in which the second wavelet filter performs filtering on the respiration and heart rate waveforms are the respiration and heart rate frequencies, which are initially estimated, respectively; two bandwidths of the second wavelet filter are respectively smaller than the two bandwidths of the first wavelet filter.

4. The method according to claim 2, wherein the final respiration and heart rate frequencies are determined specifically as follows:

normalizing reconstructed respiration and heart rate waveform signals to obtain the corresponding one-dimensional data;

inputting the one-dimensional data into the trained one-dimensional CNN, and estimating the respiration and heart rate frequencies again, wherein the one-dimensional CNN comprises three sub-modules: the first sub-module contains two one-dimensional convolutional layers, after each of convolutional layers, an activation function, a maximum pooling, and a random deactivation operation are performed sequentially; the second sub-module is connected after the first sub-module, which contains five one-dimensional convolutional layers, after each of the convolutional layers, the activation function, the maximum pooling, and the random deactivation operations are performed sequentially; the third sub-module is connected behind the second sub-module, and after a global average pooling and the random deactivation operation are performed sequentially, a frequency estimation is performed through a fully connected layer containing a single neuron, and the respiration and heart rate frequencies are estimated again;

using a two-dimensional CWT to convert the respiration and heart rate waveforms into two-dimensional CWT spectrograms; dividing the two-dimensional CWT spectrograms into a training set and a test set, and using the training set to train top layer parameters of the two-dimensional CNN, wherein underlying parameters of the two-dimensional CNN adopt an initial value before training, and the test set is adopted to verify the trained two-dimensional CNN's performance in identifying respiration and heart rate frequencies; the underlying parameters make full use of extensive and rich feature representation capabilities of the two-dimensional CNN learned from millions of the images; the top layer parameters are trained using the generated two-dimensional CWT spectrograms to estimate the respiration and heart rate frequencies based on the spectrograms;

inputting the respiration and heart rate frequencies estimated by the two CNNs into the integrated learning model, optimizing the respiration and heart rate frequencies, and determining the final respiration and heart rate frequencies.

5. The method according to claim 2, wherein the fatigue state of the human body is classified specifically as follows:

extracting the time-domain feature, the frequency-domain feature and the nonlinear feature of the respiration and heart rate from the respiration and heart rate waveforms reconstructed twice;

performing feature concatenation, default value processing and feature normalization on the extracted time-domain feature, the frequency-domain feature and the nonlinear feature of the respiration and heart rate with the final respiration and heart rate frequencies, which are finally determined, then using a latent semantic analysis to extract new features from the normalized features;

inputting the new features into a fatigue classifier constructed based on XGBoost, which categorizes the user's condition into two distinct states: fatigue state and non-fatigue state.

6. The method according to claim 1, wherein the respiration and heart rate waveforms are reconstructed specifically as follows:

filtering the rPPG raw signal by using the first wavelet filter, wherein the center frequencies of the respiration and heart rate are 0.3 Hz and 1.4 Hz, respectively; a bandwidth center of the first wavelet filter to filter a respiration signal is a respiration center frequency, a bandwidth center for filtering a heart rate signal is a center frequency of the heart rate;

performing inverse continuous wavelet transform (ICWT) on the filtered respiration and heart rate signals to obtain the initially reconstructed respiration and heart rate waveforms;

on basis of waveform peak-seeking and valley-seeking, initially estimating the respiration frequency by calculating a peak-to-peak interval of the initially reconstructed respiration waveform, calculating a peak-to-peak interval of the initially reconstructed heart rate waveform to initially estimate the heart rate frequency;

filtering the initially reconstructed respiration and heart rate waveforms by using the second wavelet filter to obtain the restructured respiration and heart rate waveforms, wherein center frequencies of two bandwidths in which the second wavelet filter performs filtering on the respiration and heart rate waveforms are the respiration and heart rate frequencies, which are initially estimated, respectively; two bandwidths of the second wavelet filter are respectively smaller than the two bandwidths of the first wavelet filter.

7. The method according to claim 1, wherein the final respiration and heart rate frequencies are determined specifically as follows:

normalizing reconstructed respiration and heart rate waveform signals to obtain the corresponding one-dimensional data;

inputting the one-dimensional data into the trained one-dimensional CNN, and estimating the respiration and heart rate frequencies again, wherein the one-dimensional CNN comprises three sub-modules: the first sub-module contains two one-dimensional convolutional layers, after each of convolutional layers, an activation function, a maximum pooling, and random deactivation operations are performed sequentially; the second sub-module is connected after the first sub-module, which contains five one-dimensional convolutional layers, after each of the convolutional layers, the activation function, the maximum pooling, and the random deactivation operations are performed sequentially; the third sub-module is connected behind the second sub-module, and after a global average pooling and the random deactivation operation are performed sequentially, a frequency estimation is performed through a fully connected layer containing a single neuron, and the respiration and heart rate frequencies are estimated again;

using a two-dimensional CWT to convert the respiration and heart rate waveforms into two-dimensional CWT spectrograms; dividing the two-dimensional CWT spectrograms into a training set and a test set, and using the training set to train top layer parameters of the two-dimensional CNN, wherein underlying parameters of the two-dimensional CNN adopt an initial value before training, and the test set is adopted to verify the trained two-dimensional CNN's performance in identifying respiration and heart rate frequencies; the underlying parameters make full use of extensive and rich feature representation capabilities of the two-dimensional CNN learned from millions of the images; the top layer parameters are trained using the generated two-dimensional CWT spectrograms to estimate the respiration and heart rate frequencies based on the spectrograms;

inputting the respiration and heart rate frequencies estimated by the two CNNs into the integrated learning model, optimizing the respiration and heart rate frequencies, and determining the final respiration and heart rate frequencies.

8. The method according to claim 1, wherein the fatigue state of the human body is classified specifically as follows:

extracting the time-domain feature, the frequency-domain feature and the nonlinear feature of the respiration and heart rate from the respiration and heart rate waveforms reconstructed twice;

performing feature concatenation, default value processing and feature normalization on an extracted time-domain feature, the frequency-domain feature and the nonlinear feature of the respiration and heart rate with the final respiration and heart rate frequencies, which are finally determined, then using a latent semantic analysis to extract new features from the normalized features;

inputting the new features into a fatigue classifier constructed based on XGBoost, which categorizes the user's condition into two distinct states: fatigue state and non-fatigue state.

9. A non-contact fatigue detection system based on rPPG, comprising:

a human face video determination unit, which is configured to determine an image video of a human face;

an rPPG signal extraction unit, which is configured to perform a human face tracking using a region-of-interest (ROI) on each image in the image video, extract a skin binarized image of a ROI of the human face; convert each of the images into an LUV color space image on basis of removing eyes and mouth regions; perform an AND operation on the skin binarized image and the LUV color space image to obtain an LUV color space image containing only human face skin information; determine a mean value of effective pixels of the LUV color space image containing only the human face skin information in each of the images, use a mean value curve of the effective pixels corresponding to the image video as a raw signal of the human face rPPG;

a waveform reconstruction unit, which is configured to filter an rPPG raw signal by using a first wavelet filter with a bandwidth established around a center frequency that corresponds separately to a respiration rate and a heart rate, remove a noise in a coarse-grained manner, initially reconstruct respiration and heart rate waveforms, wherein the bandwidth of the first wavelet filter is greater than a preset threshold; calculate a human body's average respiration and heartbeat intervals based on initially reconstructed respiration and heart rate waveforms to initially estimate respiration and heart rate frequencies, and filter the initially reconstructed respiration and heart rate waveforms by using a second wavelet filter with a bandwidth set based on the respiration and heart rate frequencies, which are initially estimated, remove the noise in a fine-grained manner to obtain reconstructed respiration and heart rate waveforms, wherein the bandwidth of the second wavelet filter is smaller than the bandwidth of the first wavelet filter;

a frequency determination unit, which is configured to input a one-dimensional data of the reconstructed respiration and heart rate waveforms into a trained one-dimensional CNN to estimate the respiration and heart rate frequencies again; transform the one-dimensional data of the reconstructed respiration and heart rate waveforms by CWT into two-dimensional CWT spectrograms, input the two-dimensional CWT spectrograms into a trained two-dimensional CNN to further estimate the respiration and heart rate frequencies; input the respiration and heart rate frequencies estimated by two CNNs into an integrated learning model to determine final respiration and heart rate frequencies;

a fatigue detection unit, which is configured to extract a time-domain feature, a frequency-domain feature and a nonlinear feature of the corresponding respiration and heart rate based on the respiration and heart rate waveforms reconstructed twice, concatenate extracted features and a final determined respiration and heart rate frequency and inputting the extracted features and the final determined respiration and heart rate frequency into a trained classifier, classify a fatigue state of a human body, and detect the fatigue state of the human body.

10. The system according to claim 9, wherein the rPPG signal extraction unit determines each of the images in the image video of the human face, performs a human face detection and a human face alignment operation on each of the images, and extracts the ROI of the human face; converts a RGB image in the ROI of the human face in each of the images into a YCbCr color space, and extracts the skin binarized image of the ROI of the human face; wherein the skin binarized image is: setting pixels related to skin to 1, and setting pixels, which are not related to the skin, to 0; with respect to each of the images in the image video, removes noises, which are not related to the skin, and deletes the eyes and mouth regions of the human face based on human face feature points, performs a conversion from the RGB image to the LUV color space, and obtains an LUV color space image of each of the images; performs the AND operation on the skin binarized image of the ROI of the human face in each of the images and the LUV color space image of each of the images to obtain the LUV color space image containing only the skin information; calculates the mean value of the effective pixels of the LUV color space image containing only the skin information in each of the images, and uses a time-series change curve of the mean value of the effective pixels as the rPPG raw signal.

11. The system according to claim 10, wherein the waveform reconstruction unit filters the rPPG raw signal by using the first wavelet filter, wherein the center frequencies of the respiration and heart rate are 0.3 Hz and 1.4 Hz, respectively; a bandwidth center of the first wavelet filter to filter a respiration signal is a respiration center frequency, a bandwidth center for filtering a heart rate signal is a center frequency of the heart rate; performs ICWT on the filtered respiration and heart rate signals to obtain the initially reconstructed respiration and heart rate waveforms; on basis of waveform peak-seeking and valley-seeking, initially estimates the respiration frequency by calculating a peak-to-peak interval of the initially reconstructed respiration waveform, calculates a peak-to-peak interval of the initially reconstructed heart rate waveform to initially estimate the heart rate frequency; filters the initially reconstructed respiration and heart rate waveforms by using the second wavelet filter to obtain the restructured respiration and heart rate waveforms, wherein center frequencies of two bandwidths in which the second wavelet filter performs filtering on the respiration and heart rate waveforms are respiration and heart rate frequencies, which are initially estimated, respectively; two bandwidths of the second wavelet filter are respectively smaller than the two bandwidths of the first wavelet filter.

12. The system according to claim 10, wherein the frequency determination unit normalizes reconstructed respiration and heart rate waveform signals to obtain the corresponding one-dimensional data; inputs the one-dimensional data into the trained one-dimensional CNN, and estimates the respiration and heart rate frequencies again, wherein the one-dimensional CNN comprises three sub-modules: the first sub-module contains two one-dimensional convolutional layers, after each of convolutional layers, an activation function, a maximum pooling, and a random deactivation operation are performed sequentially; the second sub-module is connected behind the first sub-module, which contains five one-dimensional convolutional layers, after each of the convolutional layers, the activation function, the maximum pooling, and the random deactivation operations are performed sequentially; the third sub-module is connected behind the second sub-module, and after a global average pooling and the random deactivation operation are performed sequentially, a frequency estimation is performed through a fully connected layer containing a single neuron, and the respiration and heart rate frequencies are estimated again; uses the two-dimensional CWT to convert the respiration and heart rate waveforms into two-dimensional CWT spectrograms; divides the two-dimensional CWT spectrograms into a training set and a test set, and uses the training set to train top layer parameters of the two-dimensional CNN, wherein underlying parameters of the two-dimensional CNN adopt an initial value before training, and the test set is adopted to verify the trained two-dimensional CNN's performance in identifying respiration and heart rate frequencies; the underlying parameters make full use of extensive and rich feature representation capabilities of the two-dimensional CNN learned from millions of the images; the top layer parameters are trained using the generated two-dimensional CWT spectrograms to estimate the respiration and heart rate frequencies based on the spectrograms; inputs the respiration and heart rate frequencies estimated by the two CNNs into the integrated learning model, optimizes the respiration and heart rate frequencies, and determines the final respiration and heart rate frequencies.

13. The system according to claim 10, wherein a fatigue detection unit extracts the time-domain feature, the frequency-domain feature and the nonlinear feature of the respiration and heart rate from the respiration and heart rate waveforms reconstructed twice; performs feature concatenation, default value processing and feature normalization on the extracted time-domain feature, the frequency-domain feature and the nonlinear feature of the respiration and heart rate with the final respiration and heart rate frequencies, which are finally determined, then uses a latent semantic analysis to extract new features from the normalized features; inputs the new features into a fatigue classifier constructed based on XGBoost to categorize the user's condition into two distinct states: fatigue state and non-fatigue state.

14. The system according to claim 9, wherein the waveform reconstruction unit filters the rPPG raw signal by using the first wavelet filter, wherein the center frequencies of the respiration and heart rate are 0.3 Hz and 1.4 Hz respectively; a bandwidth center of the first wavelet filter to filter a respiration signal is a respiration center frequency, a bandwidth center for filtering a heart rate signal is a center frequency of the heart rate; performs ICWT on the filtered respiration and heart rate signals to obtain the initially reconstructed respiration and heart rate waveforms; on basis of waveform peak-seeking and valley-seeking, initially estimates the respiration frequency by calculating a peak-to-peak interval of the initially reconstructed respiration waveform, calculates a peak-to-peak interval of the initially reconstructed heart rate waveform to initially estimate the heart rate frequency; filters the initially reconstructed respiration and heart rate waveforms by using the second wavelet filter to obtain the restructured respiration and heart rate waveforms, wherein center frequencies of two bandwidths in which the second wavelet filter performs filtering on the respiration and heart rate waveforms are respiration and heart rate frequencies, which are initially estimated, respectively; two bandwidths of the second wavelet filter are respectively smaller than the two bandwidths of the first wavelet filter.

15. The system according to claim 9, wherein the frequency determination unit normalizes reconstructed respiration and heart rate waveform signals to obtain the corresponding one-dimensional data; inputs the one-dimensional data into the trained one-dimensional CNN, and estimates the respiration and heart rate frequencies again, wherein the one-dimensional CNN comprises three sub-modules: the first sub-module contains two one-dimensional convolutional layers, after each of convolutional layers, an activation function, a maximum pooling, and a random deactivation operation are performed sequentially; the second sub-module is connected behind the first sub-module, which contains five one-dimensional convolutional layers, after each of the convolutional layers, the activation function, the maximum pooling, and the random deactivation operations are performed sequentially; the third sub-module is connected behind the second sub-module, and after a global average pooling and the random deactivation operation are performed sequentially, a frequency estimation is performed through a fully connected layer containing a single neuron, and the respiration and heart rate frequencies are estimated again; uses the two-dimensional CWT to convert the respiration and heart rate waveforms into two-dimensional CWT spectrograms; divides the two-dimensional CWT spectrograms into a training set and a test set, and uses the training set to train top layer parameters of the two-dimensional CNN, wherein underlying parameters of the two-dimensional CNN adopt an initial value before training, and the test set is adopted to verify the trained two-dimensional CNN's performance in identifying respiration and heart rate frequencies; the underlying parameters make full use of extensive and rich feature representation capabilities of the two-dimensional CNN learned from millions of the images; the top layer parameters are trained using the generated two-dimensional CWT spectrograms to estimate the respiration and heart rate frequencies based on the spectrograms; inputs the respiration and heart rate frequencies estimated by the two CNNs into the integrated learning model, optimizes the respiration and heart rate frequencies, and determines the final respiration and heart rate frequencies.

16. The system according to claim 9, wherein a fatigue detection unit extracts the time-domain feature, the frequency-domain feature and the nonlinear feature of the respiration and heart rate from the respiration and heart rate waveforms reconstructed twice; performs feature concatenation, default value processing and feature normalization on a extracted time-domain feature, the frequency-domain feature and the nonlinear feature of the respiration and heart rate with the final respiration and heart rate frequencies, which are finally determined, then uses a latent semantic analysis to extract new features from the normalized features; inputs the new features into a fatigue classifier constructed based on XGBoost, which categorizes the user's condition into two distinct states: fatigue state and non-fatigue state.

* * * * *